(12) United States Patent
Xie et al.

(10) Patent No.: US 7,322,932 B2
(45) Date of Patent: Jan. 29, 2008

(54) METHOD FOR SUTURELESSLY ATTACHING A BIOMATERIAL TO AN IMPLANTABLE BIOPROSTHESIS FRAME

(75) Inventors: Hua Xie, Portland, OR (US); Lisa A. Buckley, New York, NY (US)

(73) Assignee: Providence Health System - Oregon, Seattle, WA (US)

( * ) Notice: Subject to any disclaimer, the term of this patent is extended or adjusted under 35 U.S.C. 154(b) by 648 days.

(21) Appl. No.: 10/770,978

(22) Filed: Feb. 2, 2004

(65) Prior Publication Data

US 2005/0021136 A1 Jan. 27, 2005

Related U.S. Application Data

(62) Division of application No. 10/104,499, filed on Mar. 21, 2002, now Pat. No. 7,163,556.

(51) Int. Cl.
*A61F 2/04* (2006.01)
(52) U.S. Cl. ...................................................... 600/36
(58) Field of Classification Search ........ 623/1.1–2.42, 623/901; 600/36; 128/898
See application file for complete search history.

(56) References Cited

U.S. PATENT DOCUMENTS

| | | | |
|---|---|---|---|
| 5,370,685 A * | 12/1994 | Stevens | ................ 623/2.11 |
| 5,469,868 A * | 11/1995 | Reger | ................ 128/898 |
| 5,571,216 A | 11/1996 | Anderson | |
| 5,693,085 A | 12/1997 | Buirge et al. | |
| 5,697,969 A | 12/1997 | Schmitt et al. | |
| 5,925,078 A | 7/1999 | Anderson | |
| 6,077,296 A * | 6/2000 | Shokoohi et al. | ......... 623/1.11 |
| 6,087,552 A | 7/2000 | Gregory | |
| 6,126,686 A * | 10/2000 | Badylak et al. | ............ 623/1.24 |
| 6,187,039 B1 | 2/2001 | Hiles et al. | |
| 6,206,931 B1 | 3/2001 | Cook et al. | |
| 6,494,904 B1 | 12/2002 | Love | |
| 2001/0039450 A1 | 11/2001 | Pavcnik et al. | |
| 2002/0173842 A1 | 11/2002 | Buchanan | |

* cited by examiner

*Primary Examiner*—Samuel G. Gilbert
(74) *Attorney, Agent, or Firm*—Marger Johnson & McCollom, P.C.

(57) ABSTRACT

A bioprosthetic valve graft comprises a valve frame and valve flaps, the latter acting to open or close a valve aperture to directionally control fluid flow through the bioprosthesis. The bioprosthetic valve graft comprises method for suturelessly attaching a biomaterial suturelessly bonded to the A method for securing a biomaterial to a valve frame includes positioning a flexible valve frame defining an open area on a first major surface of a biomaterial sheet having a peripheral edge, wherein positioning serves to approximate the valve frame and the peripheral edge of the biomaterial sheet to form an at least first bonding locus; and suturelessly bonding the biomaterial to the valve frame at the at least first bonding locus. The method avoids the disadvantages associated with conventional sutures and substantially reduces medical complications in implantations.

45 Claims, 4 Drawing Sheets

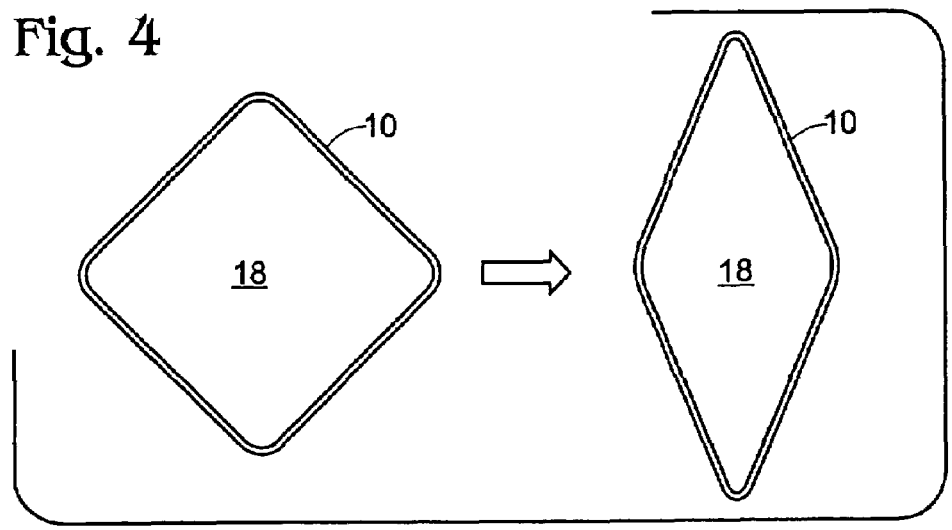
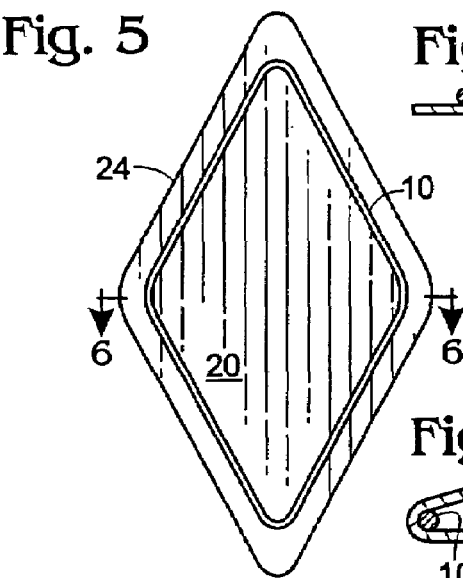
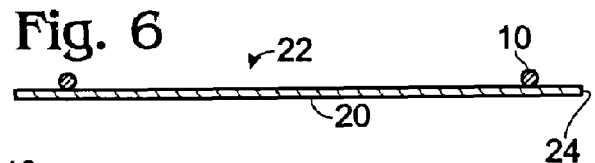
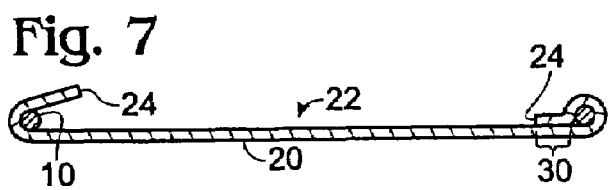
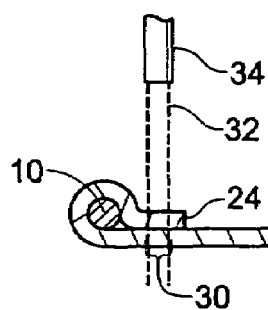

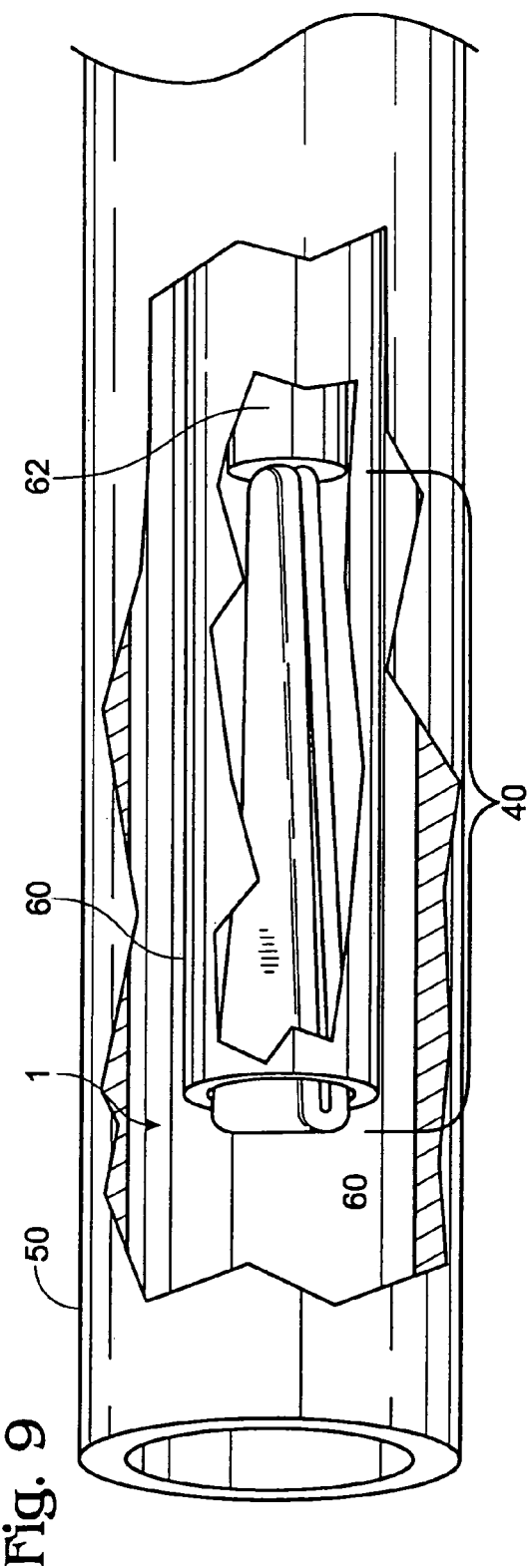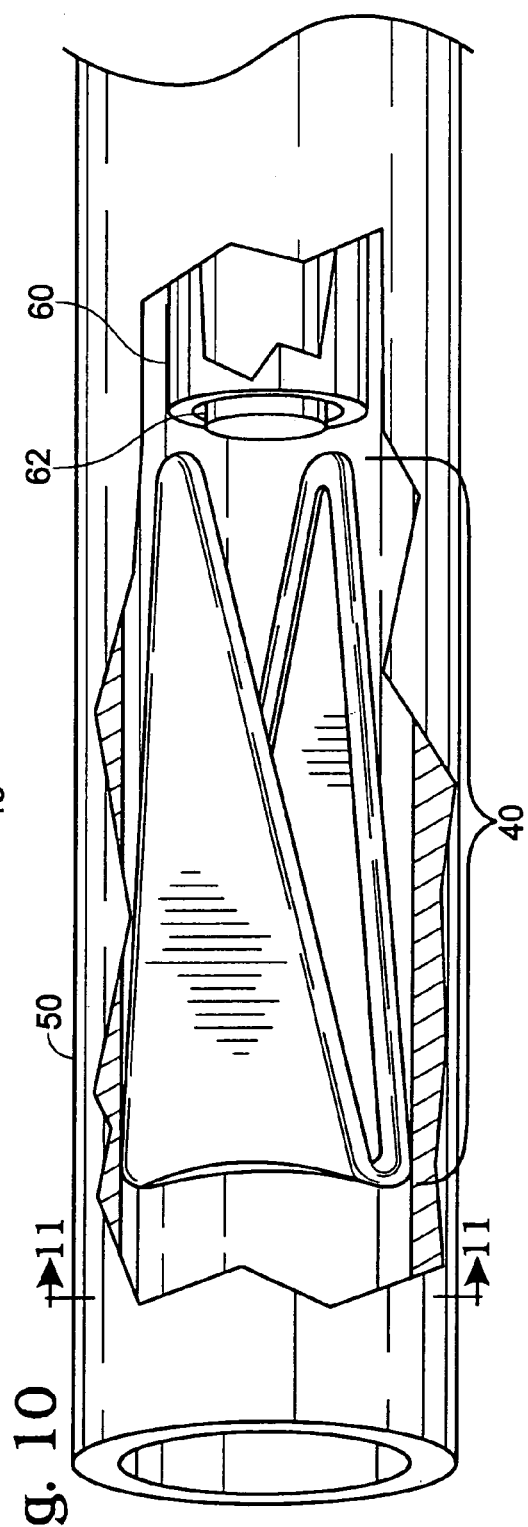

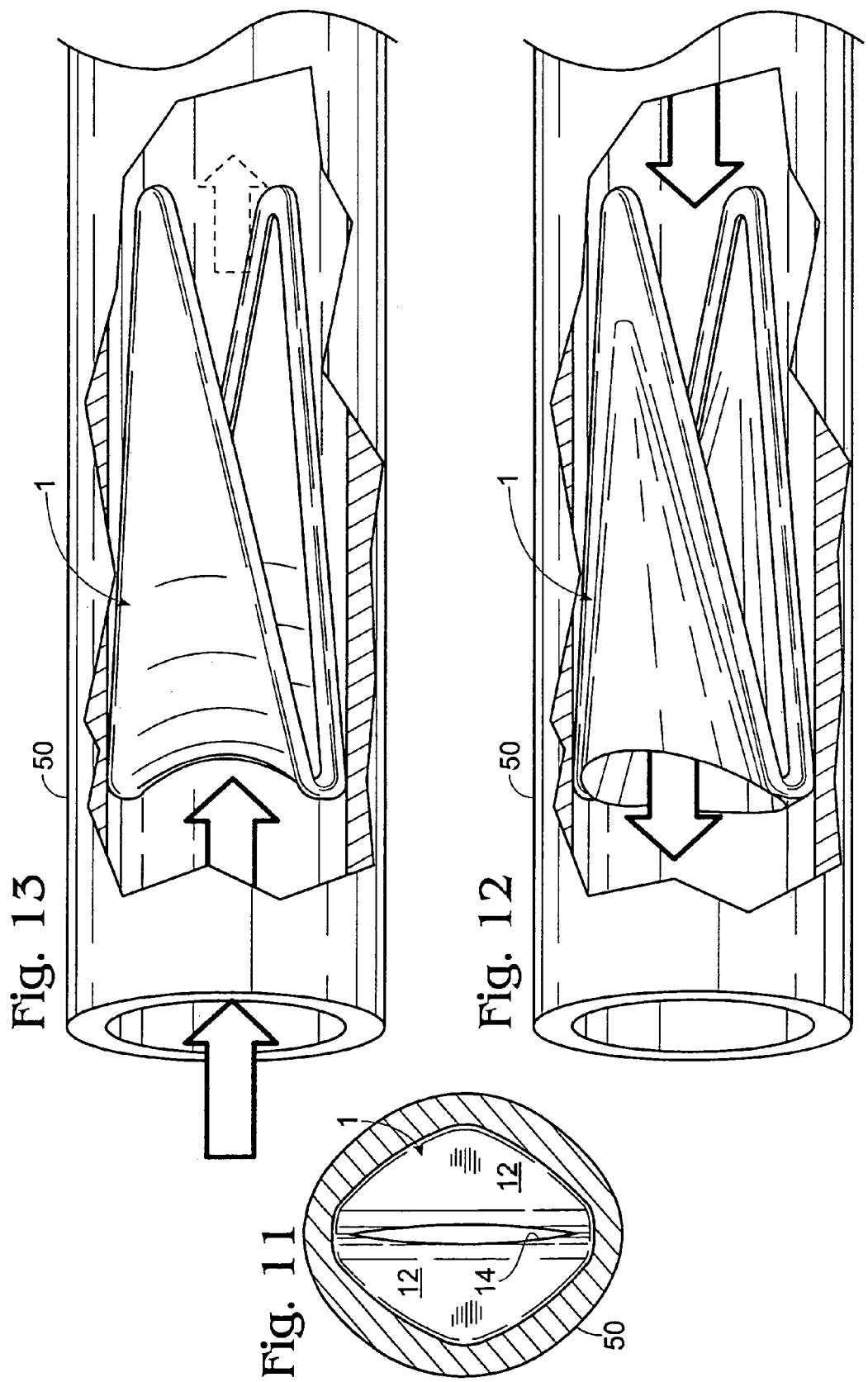

METHOD FOR SUTURELESSLY ATTACHING A BIOMATERIAL TO AN IMPLANTABLE BIOPROSTHESIS FRAME

RELATED APPLICATION DATA

This application is a division of U.S. Ser. No. 10/104,499, filed on Mar. 21, 2002, now U.S. Pat. No. 7,163,556, issued Jan. 16, 2007.

STATEMENT OF GOVERNMENT RIGHTS

This invention was made with the U.S. Government support under Grant Number DAMD17-96-1-6006, awarded by the Army Medical Research and Materiel Command. The U.S. Government may have certain rights in the invention.

BACKGROUND OF THE INVENTION

The present disclosure is related to the field of artificial valves, and more specifically to an implantable, sutureless valve graft comprising a biomaterial. The disclosure is further related to a method for suturelessly bonding a biomaterial to a bioprosthetic frame.

Prosthetic stents and valves have been described in the prior art. Stents have been used with success to overcome the problems of restenosis or re-narrowing of a vessel wall. Valves are exemplified by U.S. Pat. No. 5,258,023 (to Roger), in which a prosthetic valve is taught that is constructed of synthetic materials.

However, the use of such devices is often associated with thrombosis and other complications. Additionally, prosthetic devices implanted in vascular vessels can exacerbate underlying atherosclerosis.

Research has focused on trying to incorporate artificial materials or biocompatible materials as bioprosthesis coverings to reduce the untoward effects of metallic device implantation. Such complications include intimal hyperplasia, thrombosis and lack of native tissue incorporation.

Synthetic materials for stent coverings vary widely, e.g., synthetic materials such as Gore-Tex®, polytetrafluoroethylene (PTFE), and a resorbable yarn fabric (U.S. Pat. No. 5,697,969 to Schmitt et al.). Synthetic materials generally are not preferred substrates for cell growth.

Biomaterials and biocompatible materials also have been utilized in prostheses. Such attempts include a collagen-coated stent, taught in U.S. Pat. No. 6,187,039 (to Hiles et al.). As well, elastin has been identified as a candidate biomaterial for covering a stent (U.S. Pat. No. 5,990,379 (to Gregory)).

In contrast to synthetic materials, collagen-rich biomaterials are believed to enhance cell repopulation and therefore reduce the negative effects of metallic stents. It is believed that small intestinal submucosa (SIS) is particularly effective in this regard.

Bioprosthetic valves combining synthetic and biological materials have also been studied. For example, U.S. Pat. No. 5,824,06 (to Lemole); U.S. Pat. No. 6,350,282 (to Eberhardt); and U.S. Pat. No. 5,928,281 (to Huynh) teach bioprosthetic heart valves that may employ an aortic valve (comprising animal or patient tissue) sutured to an artificial valve frame.

Some of the above-discussed coverings, while used to prevent untoward effects, actually exacerbate the effects to some extent. Accordingly, it is desirable to employ a native biomaterial or a biocompatible material to reduce post-procedural complications.

A mechanically hardier valve graft device is required in certain implantation sites, such as cardiac, aortic, or other cardiovascular locations. In order to produce a sturdier bioprosthesis, a plurality of layers of biomaterial may be used. Suturing is a poor technique for joining multiple layers of biomaterial. While suturing is adequate to join the biomaterial sheets to the metallic frame, the frame-sutured multiple sheets are not joined on their major surfaces and are therefore subject to leakage between the layers. Suturing of the major surfaces of the biomaterial layers introduces holes into the major surfaces, increasing the risk of conduit fluid leaking through or a tear forming in one of the surfaces.

Heretofore, biomaterials have been attached to bioprosthetic frames, e.g., stents and valves, using conventional suturing techniques. As well, the primary methods available for securing prostheses to tissue (or tissue to tissue) involved the use of sutures or staples. However, this approach is disadvantageous from manufacturing and implantation perspectives.

Suturing is time-consuming and labor-intensive. For example, suturing a sheet of biomaterial over a stent frame typically is an operator-dependent process that can take up to two hours for trained personnel. Because suturing is manually performed, there are concerns relating to manufacturing uniformity and product reliability. As well, suturing entails repeatedly puncturing the biomaterial, creating numerous tiny holes that can weaken the biomaterial and potentially lead to leakage and infection after the graft device has been installed.

Moreover, the presence of suture material can enhance the foreign body response by the host patient, leading to a narrowing of the tubular vessel in which the graft is implanted.

A recent attempt to provide a "sutureless" heart valve prosthesis, U.S. Pat. No. 6,287,339 (to Vazquez, et al.), while providing a valve device to be attached to patient tissue without the use of sutures, nevertheless continues to require sutures to secure the active portion of the prosthesis to its abutment structure.

Biocompatible adhesive compounds and photochemical cross-linking agents have been investigated as alternatives to suturing. For example, fibrin glue, a fibrinogen polymer polymerized with thrombin, has been used as a tissue sealant and hemostatic agent.

Bioadhesives generally produce rigid, inflexible bond regions that can lead to local biomaterial tears and failure of the graft device. In addition, some bioadhesives and photochemical cross-linking agents carry risk of acute and chronic toxicity and bio-incompatibility.

The invention will become more readily apparent from the following detailed description, which proceeds with reference to the drawings, in which:

BRIEF DESCRIPTION OF DRAWINGS

FIG. 4 is a top view of one embodiment of a valve frame before and after a distorting force is applied to distort the frame into a flexed state.

FIG. 5 is a top view of the flexed-state valve frame placed on a sheet of biomaterial.

FIG. 6 is a cross-sectional side view of the valve frame and biomaterial taken through line 6-6 in FIG. 5.

FIG. 7 is a view of the cross-section of FIG. 6, showing folding of the edge of the biomaterial sheet over the wire frame.

FIG. 8 is a view of the cross-section of FIGS. 6-7, showing one embodiment of sutureless bonding of the edge of the biomaterial sheet to the first major surface of the sheet at a first bonding locus.

FIG. 9 is a cutaway perspective view diagram of one embodiment of a method for implanting a valve graft employing a catheter to introduce the folded valve graft to an implantation site in a patient's tubular vessel.

FIG. 10 is a cutaway perspective view diagram showing a valve graft introduced into a tubular vessel by a catheter.

FIG. 11 is an axial view down the tubular vessel of FIGS. 9-10 from reference line 11-11, showing the implanted valve graft.

FIGS. 12-13 are cutaway perspective views of the implanted valve graft of FIGS. 10-11, showing unidirectional flow control by the valve graft.

DETAILED DESCRIPTION OF EMBODIMENTS

Figure 1:
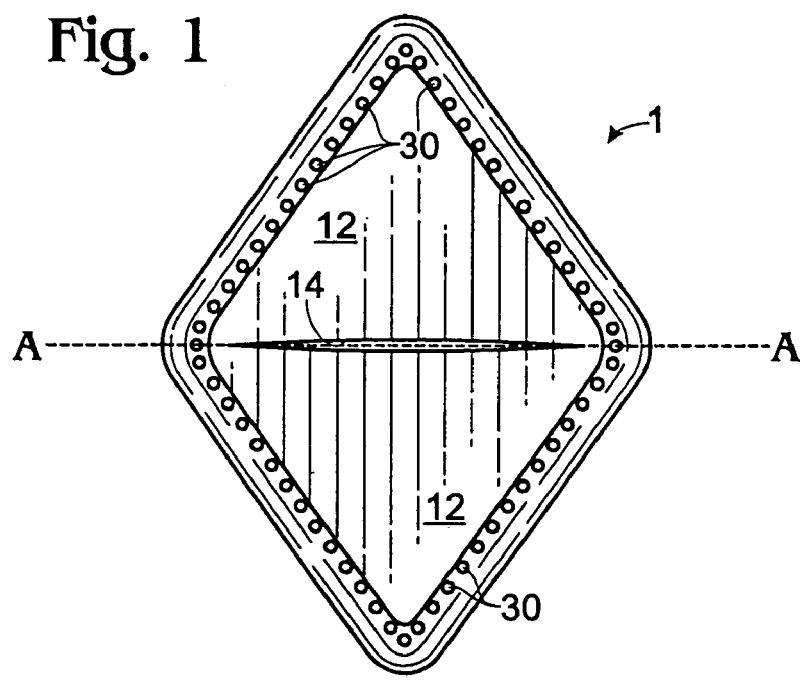
FIG. 1 is a top view of a valve graft according to the present disclosure.
Figure 2:
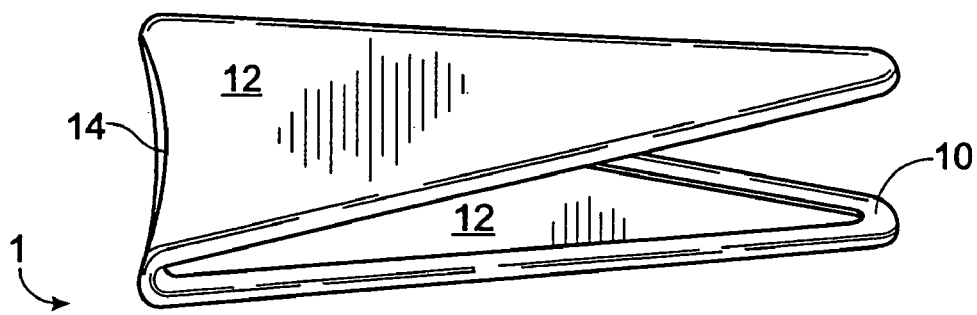
FIGS. 2-3 are perspective side and axial views, respectively, of the valve graft of FIG. 1 after folding along lin A-A in FIG. 1.
Figure 3:
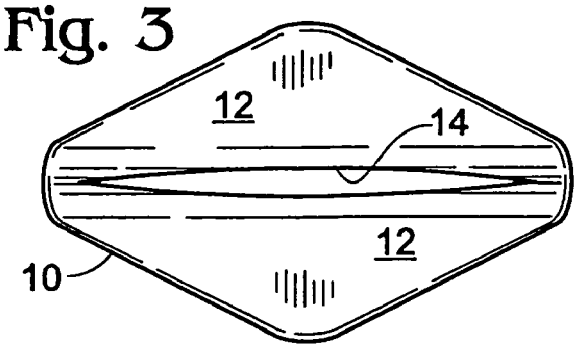

A valve graft 1 according to the present disclosure is shown in FIGS. 1-3. The valve graft generally comprises a valve frame 10 defining a valve frame open area (18 in FIG. 4). The open area is spanned by a pair of valve flaps 12 constructed of a biomaterial, discussed below. The valve flaps have positioned therebetween an aperture 14.

The valve frame 10 is preferably a closed loop and is commonly constructed of fine-gauge metal (e.g., 0.014 inch diameter), although other materials can be effectively employed. For example, the valve frame can alternatively be made of a synthetic material such as TEFLON (polytetrafluoroethylene). As well, the valve frame can be fabricated of a resorbable or biodegradable composition.

In one embodiment, the valve frame 10 is a memory wire formed into a desired shape. As illustrated herein, the valve frame is rhomboidal, although other shapes can be utilized to effect a variety of valve shapes and dimensions.

Such a shape memory wire frame is known in the art as a frame that substantially returns to its original shape after it is deformed and then released, as described in U.S. Pat. No. 4,512,338 (to Balko et al.). The alternative compositions disclosed above also can be of a memory character if desired.

The valve flaps 12 span the valve frame open area 18 and are suturelessly bonded to the valve frame 10. An aperture 14 separates the valve flaps and serves as a port through which fluid can traverse the valve graft when in use in a patient's vessel.

The valve flaps 12 preferably are of a collageneous biomaterial and can be constructed using a variety of collagen-rich biomaterials, e.g., a synthetic collagen matrix or of native tissue-derived, collagen-rich biomaterials such as pericardium, peritoneum, dura mater, fascia and bladder or ureteral acellular matrices.

An exemplary method for making the valve graft described above is shown in FIGS. 4-8. In this method, a valve frame 10 is distorted into a flexed state (FIG. 4). In this flexed state, the ratio of the long axis of the frame to its short axis is increased as compared to the base state. In the preferred embodiment wherein the frame is composed of a memory material, it should be apparent that the valve frame will therefore be under tension when flexed.

The valve frame is then placed on a first major surface 22 of a sheet of biomaterial 20 (FIGS. 5-6). A cross-section through line 6-6 of FIG. 5, corresponding to the short axis of the valve frame, is shown in FIG. 6. An edge 24 of the biomaterial 20 is folded over the valve frame 10 to contact the edge with the first major surface 22 of the biomaterial (FIG. 7) and form thereby a first bonding locus 30.

In this embodiment, the biomaterial 20 is a trimmed portion of porcine intestinal submucosa. The intestinal submucosa graft is harvested and delaminated in accordance with the description in U.S. Pat. Nos. 4,956,178 and 4,902,508 (both to Badylak et al.). An intestinal submucosa segment is thereby obtained that can be effectively used as a biomaterial sheet as described herein.

Sutureless bonding of the edge 24 of the biomaterial sheet to the first major surface 22 of the sheet is illustrated in FIG. 8. The sutureless bonding can be achieved using thermal bonding or chemical cross-linking techniques.

In thermal bonding shown in FIG. 8, the at least first bonding locus 30, in which the edge 24 of the biomaterial 20 is apposed to the first major surface 22 thereof, is irradiated with energy 32 sufficiently to heat, denature and fuse together the components of the biomaterial.

The bonding technique is preferably confined to the selected bonding loci, such that the sutureless bonding effectively "spot-welds" the biomaterial edge to the first major surface of the sheet. Alternatively, the edge can be welded to the first major surface in one or more weld lines.

In irradiating the at least first bonding locus with energy from an energy source 34, wherein the energy source is an 800 nm diode laser, propagation of laser energy is preferably directed perpendicular to the biomaterial. The biomaterial, preferably being transparent to the laser light at the chosen light wavelength, absorbs little energy and hence sustains minimal thermal damage. However, the energy-absorbing material at the at least first bonding locus absorbs energy and thereby conducts heat to the adjacent biomaterial.

Sutureless bonding using thermal energy preferably creates a weld while minimizing transfer of heat to surrounding tissues, thereby reducing collateral thermal damage. The chromophore also can aid in thermal confinement and thereby reduce denaturation of surrounding tissue.

With sufficient energy irradiation, the biomaterial edge and first major surface at the at least first bonding locus are denatured at the protein level. It is believed that the molecules in the biomaterial intertwine with one another. Upon cooling, the bond site is weld-sealed, wherein the biomaterial edge and first major surface of the biomaterial are welded together.

As has been mentioned, the valve frame alternatively can be constructed so as to comprise a biological material amenable to laser fusion techniques. With such an embodiment, the collagen-rich biomaterial sheet can be attached to the valve frame by fusion directly thereto, rather than folding the sheet around it and fusing the edge to the first major surface.

The combination of an energy-absorbing material (i.e., a chromophore, such as indocyanine green (ICG)) and an 800 nm diode laser is the preferred equipment for sutureless bonding in the method herein disclosed. The chromophore can be an endogenous or exogenous substance. The at least first bonding locus at the folded-over edge preferably includes the chromophore, either by treatment of the biomaterial before sutureless bonding or by topical application of a chromophore during sutureless bonding.

Thermal bonding can be accomplished according to either of two models. In a first model as discussed above, a device is remotely employed to generate heat within the biomaterial. A second thermal bonding model involves contacting a device with the at least first bonding locus for direct generation of heat at the biomaterial contact site. Such devices for contact-heating are known in the art and include a contact thermo-electric transducer.

In a first alternative sutureless bonding model, the biomaterial edge can be bonded to the first major surface by photo-chemical cross-linking. In a first embodiment of this technique, methylene blue is introduced to the at least first bonding locus and the region is irradiated with white light or other non-collimated light.

Conventional chemical or photo-crosslinking agents frequently present toxicity concerns if introduced into a patient. For this reason, it is preferable that such agents be avoided or the valve graft well rinsed to remove as much of the agent as possible. Methylene blue is a preferred substance for photochemical cross-linking as described above, because the dye has been shown to be easily rinsed from collagen-rich biomaterials such as SIS.

The sutureless bonding technique used can vary according to desired locus size, biomaterial, speed, cost, and procedural considerations. In all cases, however, it is apparent that the disclosed method avoids the use of sutures to attach the biomaterial to the prosthesis frame.

Sutureless bonding as disclosed herein possesses a satisfactory bond strength to permit the valve graft to be implanted into a patient's tubular vessel without increasing the risk of bond failure over that of conventional sutured attachment schemes. As has been mentioned, the presence of sutures at an implantation site increases the probability of post-procedure complications, such as foreign body reaction, thrombogenesis, leakage and reflux of fluid. Use of the sutureless bonding method therefore produces a valve graft more readily received by a patient's body.

The present method results in thermal fusion of the biomaterial to generate a strong bond. As well, the resulting valve graft provides a high affinity, migratory, and integrative capability for host cell and tissue ingrowth. The bioprosthesis also prevents fluid leakage while retaining a soft, pliable character. Employment of a biomaterial sheath and avoidance of sutures provide a non-carcinogenic valve stent that greatly minimizes calcification and foreign body reactions.

An aperture 14 is formed in the biomaterial sheet 20, creating the bidentate valve graft shown herein. The width of the aperture can be varied to control the flexibility of the valve and the maximum flow rate through the valve.

FIGS. 9-10 are diagrams of one embodiment of a method for implanting a valve graft 1 at an implantation site 40 in a patient's tubular vessel 50. The valve graft 1 first is folded along one axis (i.e., along reference line A-A in FIG. 1), bringing proximate the distal corners of the frame.

The biomaterial sheet typically is stretched thereby and preferably curves below the short axis and toward the distal corners, taking on a saddle-like shape. Owing to both the composition of the valve frame and the tensile strength of the biomaterial, tension on the biomaterial is not so great as to tear the biomaterial or to pull open the aperture.

A catheter 60 is preferably employed to introduce the folded valve graft to the implantation site. The valve graft 1 is sufficiently tightly folded to permit the valve graft to be placed within the catheter 60. This fitment is generally achieved by bringing the distal corners closer and also compressing the frame along the fold axis. The resultant folded valve graft has a high aspect ratio relative to its relaxed orientation (i.e., as shown in FIG. 9).

The catheter 60 is then maneuvered to position the distal tip thereof at the implantation site 40, such as in a vein 50. The tightly-folded valve graft is introduced into the vein or other tubular vessel by deployment from the distal tip of the catheter 60, as shown in FIG. 10. Such release can be achieved by pushing the valve graft from inside the catheter with a ramrod-type element 62, such as a guidewire.

Upon release from the catheter, the valve graft will tend to spring back to its original conformation, limited by the walls of the tubular vessel (FIGS. 10-11, with the valve aperture shown open). This expanding tendency is due to the shape memory material of which the valve frame is constructed.

The valve graft will remain at the implantation site in a folded state, though not so tightly folded as in FIG. 9. Over time, native tissue overgrowth occurs, further anchoring the valve graft in place.

A collagen-rich biomaterial sheet can serve as a layer(s) (single or multiple sheets) applied to a supporting structure (e.g., valve frame) to control fluid flow direction through the conduit while preventing leakage out of the conduit. Such valve grafts might be used, for example, in the cardiovascular system (blood vessels), gastrointestinal tract, urinary tract, and trachea FIGS. 12-13 show simplified views of the implanted valve graft of FIGS. 10-11, illustrating unidirectional flow control via valve action. For purposes of explanation, it will be assumed that a valve graft has been implanted in a vein of a patient.

It should be noted that the flaps 12 or leaflets of the valve graft 1 have a flexible character imparted by the composition of the biomaterial sheet 20. The flaps 12 therefore can be flexed or bowed by the force of the incident fluid. Such pliant or elastic property is known in the art for "natural tissue" valves, as opposed to mechanical valves.

In FIG. 12, anterograde blood flow in the vein 50 is occurring, consistent with normal circulation, i.e., from right to left. Pressure on the upstream surface of the valve graft flaps 12 by the blood (solid arrow) causes the flaps 12 to be bowed toward the walls of the vein 50. The valve graft aperture 14 is opened thereby, permitting the blood to flow through the valve graft 1 and further downstream (solid arrow) through the vein 50.

In retrograde blood flow to the valve (solid arrow, FIG. 13), blood fills and is trapped in the "dead-end" regions between the valve graft flaps 12 and the vein wall 50. This phenomenon, coupled with the continuing-fluid pressure on the flaps 12 caused by physiological blood flow, causes blood to contact and press on the downstream surface of the valve graft flaps, flexing them inward and away from the vessel walls 50. By bowing the flaps inward, the valve graft aperture 14 is effectively closed and retrograde flow through the valve graft is substantially prevented (dashed arrow).

A valve graft preferably is constructed in which the aperture is substantially closed when the valve graft is in a resting-state conformation (i.e., its state when implanted in a vessel having no fluid flow). Such construction is dependent on the size, shape, and dimensions of the valve frame, the presence and degree of tension that can be applied to the biomaterial sheet during valve graft fabrication, and the dimensions and orientation of the aperture.

In another alternative valve graft, the aperture can be designed to incompletely close or to substantially narrow in the face of retrograde flow, depending on the particular configuration and dimensions of the implanted valve graft.

If a partial retrograde flow is desired, for example, the aperture dimensions can be chosen to prevent complete closure of the aperture in an in situ implantation.

Implantation of a valve graft according to the present disclosure provides several benefits over prior art prostheses. Collagen and SIS are known to provide a matrix that encourages native cell repopulation and may ultimately enhance tissue repair and regeneration as well as integration of implanted supporting structure materials.

One advantage of the disclosed method for making a valve graft is that thermal bonding, and especially laser fusion of the biomaterial edge to the first major surface is a rapid technique that yields water-tight bonds. As well, laser fusion has the capability of attaching multiple biomaterial sheets at numerous locations on their major surfaces, reducing the chance of leakage between the biomaterial sheets.

Heretofore, laser fusion has not gained widespread acceptance for bonding approximated tissue edges, largely because of weak bond strength. However, laser fusion of collagen-rich biomaterials as described herein resulted in strong tissue bonds. Further, collagen-rich biomaterials have been observed to readily incorporate chromophores such as ICG, further enhancing the efficacy of laser fusion in the present invention.

Another advantage of the present valve graft over prior art prostheses is that the use of sutures is obviated in the present invention. The risk of a foreign body response is therefore substantially mitigated.

A further advantage is that a valve graft as disclosed herein and constructed with collageneous biomaterial flaps will retain the excellent bio-active properties of small intestinal submucosa graft with greatly reduced risk of cytotoxicity and foreign body reactions. The sutureless bonding welds provide sufficient mechanical and structural strength to enable the valve graft to be employed in medical procedures and to function acceptably in situ.

A person skilled in the art will be able to practice the present invention in view of the description present in this document, which is to be taken as a whole. Numerous details have been set forth in order to provide a more thorough understanding of the invention. In other instances, well-known features have not been described in detail in order not to obscure unnecessarily the invention.

While the invention has been disclosed in its preferred form, the specific embodiments presented herein are not to be considered in a limiting sense. Indeed, it should be readily apparent to those skilled in the art in view of the present description that the invention can be modified in numerous ways. The inventor regards the subject matter of the invention to include all combinations and sub-combinations of the various elements, features, functions and/or properties disclosed herein.

The invention claimed is:

1. A method for producing a sutureless valve graft suitable for physiological implantation, comprising:
    positioning a flexible valve frame defining an open area on a first major surface of a biomaterial sheet having a peripheral edge, said positioning serving to approximate the valve frame and the peripheral edge of the biomaterial sheet to form an at least first bonding locus; and
    suturelessly bonding the biomaterial to the valve frame at the at least first bonding locus;
    further comprising dehydrating the biomaterial prior to suturelessly bonding; and rehydrating the biomaterial after suturelessly bonding.

2. The method of claim 1, wherein positioning comprises:
    positioning the valve frame on the first major surface of the biomaterial sheet; and
    folding the edge of the biomaterial sheet over the valve frame so that the edge of the biomaterial sheet is contacted with the first major surface of the biomaterial sheet.

3. The method of claim 1, wherein suturelessly bonding comprises suturelessly bonding the edge of the biomaterial sheet directly to the valve frame.

4. The method of claim 1, further comprising:
    applying a distorting force to the valve frame to distort the valve frame into a flexed state prior to positioning the valve frame; and
    releasing the distorting force after suturelessly bonding.

5. The method of claim 1, wherein the biomaterial sheet consists essentially of small intestine submucosa.

6. The method of claim 1, wherein suturelessly bonding comprises irradiating the at least first bonding locus with energy sufficient to at least partially fuse the portion of the approximated biomaterial sheet to attach the biomaterial to the valve frame at the at least first bonding locus.

7. The method of claim 6, wherein irradiating the at least first bonding locus with energy comprises irradiating the at least first bonding locus with light.

8. The method of claim 7, wherein irradiating the at least first bonding locus with energy comprises irradiating the at least first bonding locus with light generated by a laser.

9. The method of claim 8, wherein irradiating the at least first bonding locus with energy comprises irradiating the at least first bonding locus with light having a wavelength of about 800 nm.

10. The method of claim 9, further comprising introducing a chromophore that is energy-absorptive at about 800 nm.

11. The method of claim 6, wherein irradiating the at least first bonding locus with energy comprises irradiating the at least first bonding locus with radio-frequency energy.

12. The method of claim 6, wherein irradiating the at least first bonding locus with energy comprises irradiating the at least first bonding locus with ultrasound energy.

13. The method of claim 1, further comprising introducing a photo-chemical crosslinking agent.

14. The method of claim 13, wherein said photo-chemical crosslinking agent is methylene blue.

15. The method of claim 14, wherein irradiating the at least first bonding locus with energy comprises irradiating the at least first bonding locus with white light.

16. The method of claim 14, wherein irradiating the at least first bonding locus with energy comprises irradiating the at least first bonding locus with ultraviolet light.

17. The method of claim 1, further comprising creating an aperture across a short axis of the biomaterial sheet.

18. The method of claim 1 wherein the biomaterial sheet comprises collagen.

19. The method of claim 1, wherein the biomaterial consists essentially of collagen.

20. A method for suturelessly attaching a collagen-rich biomaterial sheet to a prosthesis frame element, comprising:
    approximating a portion of the biomaterial sheet to the prosthesis frame element to define an at least first bonding locus; and
    irradiating the at least first bonding locus with energy from an energy-generating source, said energy sufficient to at least partially fuse the portion of the approximated biomaterial sheet;

further comprising dehydrating the biomaterial prior to bonding; and rehydrating the biomaterial after bonding.

21. The method of claim 20, wherein irradiating the at least first bonding locus with energy from an energy-generating source comprises irradiating the at least first bonding locus with energy from a radio-frequency device.

22. The method of claim 20, wherein irradiating the at least first bonding locus with energy from an energy-generating source comprises irradiating the at least first bonding locus with energy from an ultrasound device.

23. The method of claim 20, wherein irradiating the at least first bonding locus with energy from an energy-generating source comprises irradiating the at least first bonding locus with light energy from a laser.

24. The method of claim 23, wherein said laser emits light having a wavelength of about 800 nm.

25. The method of claim 23, further comprising introducing a chromophore.

26. The method of claim 25, wherein said chromophore is indocyanine green.

27. The method of claim 20, wherein irradiating the at least first bonding locus with energy from an energy-generating source comprises contacting the at least first bonding locus with a contact thermo-electric transducer.

28. The method of claim 20, wherein the prosthesis frame element comprises a synthetic material.

29. The method of claim 20, wherein the prosthesis frame element comprises a resorbable or biodegradable composition.

30. The method of claim 20, wherein the biomaterial consists essentially of collagen.

31. The method of claim 20, wherein the biomaterial substantially comprises small intestine submucosa.

32. A method for securing a biomaterial sheet to a stent frame, comprising:
    approximating a portion of the biomaterial sheet to the stent frame to define an at least first bonding locus;
    irradiating the at least first bonding locus with energy from an energy-generating source, said energy sufficient to at least partially fuse the portion of the approximated biomaterial sheet;
    at least partially dehydrating the biomaterial prior to irradiating; and
    rehydrating the at least partially dehydrated biomaterial after irradiating.

33. The method of claim 32 wherein the energy is optical energy.

34. The method of claim 33 wherein irradiating the optical energy is laser optical energy.

35. The method of claim 33 wherein the optical energy has a wavelength of about 800 nm.

36. The method of claim 35, further comprising introducing a chromophore that is energy-absorptive at about 800 nm.

37. The method of claim 33, further comprising introducing a photo-chemical crosslinking agent.

38. The method of claim 33 wherein the optical energy is white light.

39. The method of claim 33 wherein the optical energy is ultraviolet light.

40. The method of claim 32 wherein the energy is radio-frequency energy.

41. The method of claim 32 wherein the energy is ultrasound energy.

42. The method of claim 32, wherein the biomaterial consists essentially of collagen.

43. A method for producing a sutureless valve graft suitable for physiological implantation, comprising:
    positioning a flexible valve frame defining an open area on a first major surface of a biomaterial sheet having a peripheral edge, said positioning serving to approximate the valve frame and the peripheral edge of the biomaterial sheet to form an at least first bonding locus;
    suturelessly bonding the biomaterial to the valve frame at the at least first bonding locus;
    applying a distorting force to the valve frame to distort the valve frame into a flexed state prior to positioning the valve frame; and
    releasing the distorting force after suturelessly bonding.

44. The method of claim 43, further comprising securing the valve frame in the flexed state by attaching a diametric suture, wherein releasing the distorting force comprises removing the diametric suture.

45. A method for suturelessly attaching a collagen-rich biomaterial sheet to a prosthesis frame element, comprising:
    approximating a portion of the biomaterial sheet to the prosthesis frame element to define an at least first bonding locus; and
    irradiating the at least first bonding locus with energy from an energy-generating source, said energy sufficient to at least partially fuse the portion of the approximated biomaterial sheet;
    wherein the biomaterial consists essentially of collagen.

* * * * *